United States Patent
Haselby et al.

(10) Patent No.: US 9,968,337 B2
(45) Date of Patent: May 15, 2018

(54) CORING TISSUE BIOPSY NEEDLE AND METHOD OF USE

(75) Inventors: Kenneth Haselby, Battle Ground, IN (US); David Eric Orr, Piedmont, SC (US); James D. Purdy, Lafayette, IN (US); Carl Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days. days.

(21) Appl. No.: 13/325,662

(22) Filed: Dec. 14, 2011

(65) Prior Publication Data

US 2012/0157880 A1 Jun. 21, 2012

Related U.S. Application Data

(60) Provisional application No. 61/425,106, filed on Dec. 20, 2010.

(51) Int. Cl.
*A61B 10/00* (2006.01)
*A61B 17/32* (2006.01)
*A61B 10/02* (2006.01)

(52) U.S. Cl.
CPC .. *A61B 10/0233* (2013.01); *A61B 2010/0208* (2013.01)

(58) Field of Classification Search
CPC ................................................ A61B 5/00
USPC ......... 600/562, 564, 566, 567, 568; 606/167
See application file for complete search history.

(56) References Cited

U.S. PATENT DOCUMENTS

| | | | | |
|---|---|---|---|---|
| 3,692,020 | A | * | 9/1972 | Schied ........................ 600/568 |
| 3,844,272 | A | * | 10/1974 | Banko ......................... 600/566 |
| 4,177,797 | A | * | 12/1979 | Baylis et al. ................ 600/567 |
| 4,490,139 | A | * | 12/1984 | Huizenga ........... A61B 17/3417 604/264 |
| 4,708,147 | A | * | 11/1987 | Haaga ................ A61B 10/0266 600/566 |
| 4,785,826 | A | * | 11/1988 | Ward ........................... 600/567 |
| 5,047,040 | A | * | 9/1991 | Simpson et al. ............ 606/159 |
| 5,064,411 | A | * | 11/1991 | Gordon, III ....... A61B 17/0493 128/846 |
| 5,197,484 | A | * | 3/1993 | Kornberg et al. .......... 600/567 |

(Continued)

FOREIGN PATENT DOCUMENTS

| EP | 1 210 911 A2 | 6/2002 |
|---|---|---|
| EP | 1604615 A1 | 12/2005 |

(Continued)

OTHER PUBLICATIONS

Islam, Anwarul, "A New Bone Marrow Biopsy Needle With Core Securing Device," Jul. 7, 1981, pp. 359-364 (6 pages).

(Continued)

*Primary Examiner* — May Abouelela
(74) *Attorney, Agent, or Firm* — Brinks Gilson & Lione

(57) ABSTRACT

Biopsy devices and methods are provided for collecting a sufficiently-sized tissue sample from a region at a known distance by boring into the sample region using simultaneous axial and rotational movement and providing a reduced risk of: over-passing or under-passing the sample sought, injury and trauma to the surrounding tissue area, having to stick the patient more than once, sample contamination, and the user's exposure to sharps.

15 Claims, 11 Drawing Sheets

(56) References Cited

U.S. PATENT DOCUMENTS

| | | | |
|---|---|---|---|
| 5,368,045 A * | 11/1994 | Clement | A61B 10/0275 600/562 |
| 5,458,112 A | 10/1995 | Weaver | |
| 5,467,684 A * | 11/1995 | Sher | A61B 17/320758 74/129 |
| 5,505,211 A * | 4/1996 | Ohto et al. | 600/567 |
| 5,575,780 A * | 11/1996 | Saito | B24B 19/16 604/264 |
| 5,595,186 A * | 1/1997 | Rubinstein et al. | 600/567 |
| 5,655,542 A * | 8/1997 | Weilandt | 600/567 |
| 5,807,277 A * | 9/1998 | Swaim | 600/567 |
| 5,830,152 A * | 11/1998 | Tao | 600/562 |
| 5,916,229 A * | 6/1999 | Evans | 606/171 |
| 6,083,237 A * | 7/2000 | Huitema et al. | 606/180 |
| 6,213,957 B1* | 4/2001 | Milliman et al. | 600/566 |
| 6,361,504 B1* | 3/2002 | Shin | A61B 10/0233 600/562 |
| 6,875,183 B2 | 4/2005 | Cervi | |
| 7,329,227 B2* | 2/2008 | Schramm | 600/567 |
| 7,435,239 B2* | 10/2008 | Yatabe | A61M 5/158 604/272 |
| 7,513,877 B2* | 4/2009 | Viola | 600/564 |
| 7,517,321 B2* | 4/2009 | McCullough et al. | 600/566 |
| 7,959,580 B2* | 6/2011 | McCullough et al. | 600/566 |
| 7,998,086 B2* | 8/2011 | Boock et al. | 600/566 |
| 8,012,102 B2* | 9/2011 | McCullough et al. | 600/566 |
| 8,088,081 B2* | 1/2012 | Field et al. | 600/567 |
| 8,167,815 B2* | 5/2012 | Parihar | 600/564 |
| 8,170,648 B2* | 5/2012 | Field | A61B 19/54 600/431 |
| 8,187,203 B2* | 5/2012 | McClellan | A61B 10/0266 600/562 |
| 8,241,227 B2* | 8/2012 | Ohnishi et al. | 600/567 |
| 8,251,916 B2* | 8/2012 | Speeg et al. | 600/565 |
| 8,262,586 B2* | 9/2012 | Anderson et al. | 600/567 |
| 8,282,574 B2* | 10/2012 | Coonahan et al. | 600/564 |
| 8,287,465 B2* | 10/2012 | Hardin et al. | 600/565 |
| 8,475,392 B2* | 7/2013 | Hineno | A61B 10/0233 600/562 |
| 8,491,496 B2* | 7/2013 | Hibner | 600/564 |
| 8,690,793 B2* | 4/2014 | Ranpura et al. | 600/562 |
| 2001/0014778 A1 | 8/2001 | Worm et al. | 600/564 |
| 2002/0120212 A1* | 8/2002 | Ritchart et al. | 600/567 |
| 2003/0195432 A1* | 10/2003 | Kortenbach et al. | 600/562 |
| 2005/0124914 A1* | 6/2005 | Dicarlo | A61B 10/0275 600/567 |
| 2005/0165328 A1* | 7/2005 | Heske et al. | 600/566 |
| 2005/0165403 A1* | 7/2005 | Miller | 606/79 |
| 2005/0215921 A1* | 9/2005 | Hibner et al. | 600/566 |
| 2006/0030785 A1* | 2/2006 | Field et al. | 600/567 |
| 2006/0129063 A1* | 6/2006 | Thompson et al. | 600/566 |
| 2006/0167377 A1* | 7/2006 | Ritchart et al. | 600/566 |
| 2006/0276747 A1* | 12/2006 | Moos et al. | 604/117 |
| 2007/0016101 A1* | 1/2007 | Feldman | A61B 10/0275 600/567 |
| 2007/0142743 A1* | 6/2007 | Provencher et al. | 600/562 |
| 2007/0142744 A1* | 6/2007 | Provencher | 600/562 |
| 2007/0149895 A1* | 6/2007 | McCullough et al. | 600/566 |
| 2007/0167868 A1* | 7/2007 | Sauer | 600/564 |
| 2007/0213630 A1* | 9/2007 | Beckman | A61B 10/0275 600/562 |
| 2007/0276288 A1* | 11/2007 | Khaw | 600/566 |
| 2008/0234602 A1* | 9/2008 | Oostman et al. | 600/564 |
| 2008/0262383 A1 | 10/2008 | Routhier et al. | |
| 2008/0281226 A1* | 11/2008 | Peters | 600/567 |
| 2009/0204023 A1* | 8/2009 | Goldenberg | 600/567 |
| 2009/0204024 A1* | 8/2009 | Miller | 600/567 |
| 2010/0030108 A1* | 2/2010 | Anderson et al. | 600/567 |
| 2010/0160820 A1* | 6/2010 | Weikel et al. | 600/566 |
| 2010/0234760 A1* | 9/2010 | Almazan | 600/566 |
| 2011/0004121 A1* | 1/2011 | Drubetsky et al. | 600/567 |
| 2011/0313316 A1* | 12/2011 | Ranpura et al. | 600/566 |
| 2012/0010527 A1* | 1/2012 | Sundheimer et al. | 600/566 |
| 2012/0059277 A1* | 3/2012 | Field et al. | 600/567 |

FOREIGN PATENT DOCUMENTS

| | | |
|---|---|---|
| EP | 1731103 A1 | 12/2006 |
| WO | WO 83/02220 A1 | 7/1983 |

OTHER PUBLICATIONS

Mayall et al., "Improved FNA Cytology Results With a Near Patient Diagnosis Service for Non-Breast Lesions," *J. Clin Pathol*, 1998, pp. 541-544 (5 pages).

Product brochure, NeedleTech Products, Inc., Serratus™ Vertebral Biopsy Needle, Internet page dated Dec. 16, 2009 (1 page).

Product information, "Quick-Core® Endoscopic Ultrasound Needle," www.cookmedical.com/esc/dataSheet.do?id=685, printed Jan. 11, 2011 (2 pages).

Sakamoto et al., "Prospective Comparative Study of the EUS Guided 25-Gauge FNA Needle with the 19-Gauge Trucut Needle and 22-Gauge FNA Needle in Patients With Solid Pancreatic Masses," Journal of Gastroenteroloy and Hepatology, 24, 2009, pp. 384-390 (7 pages).

Siddiqui et al., "EUS-Guided FNA of Solid Pancreatic Masses: A Prospective, Randomized Trial Comparing 22-Gauge and 25-Gauge Needles," Gastrointestinal Endoscopy, vol. 70, No. 6, 2009, pp. 1093-1097 (5 pages).

Wang, Ko Pen, "Biology Sampling Techniques," American College of Chest Physicians, downloaded from chestjournal.chestpubs.org at University of Michigan, Feb. 28, 2011, 1989 by the American College of Chest Physicians (4 pages).

International Search Report for International Application No. PCT/US2011/065045, dated Mar. 29, 2012, 3 pages.

Written Opinion of the International Searching Authority for International Application No. PCT/US2011/065045, dated Mar. 29, 2012, 5 pages.

* cited by examiner

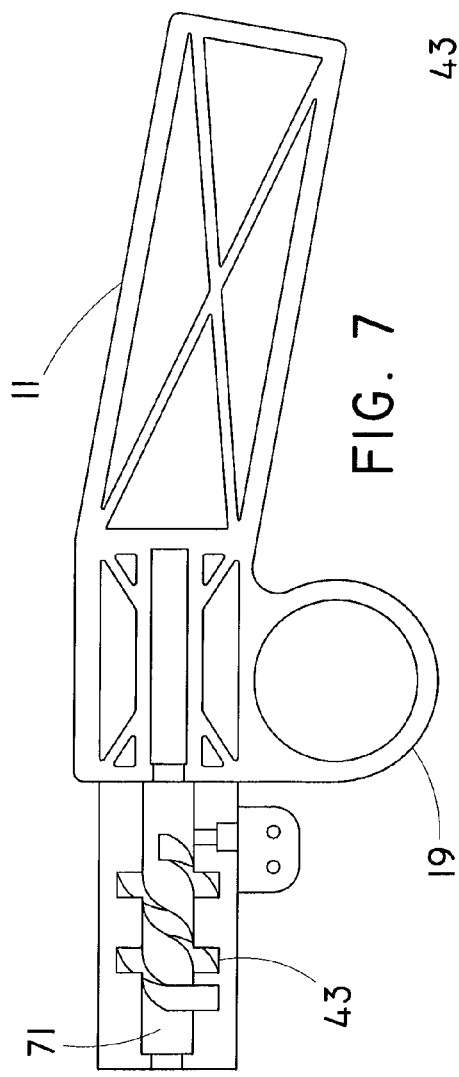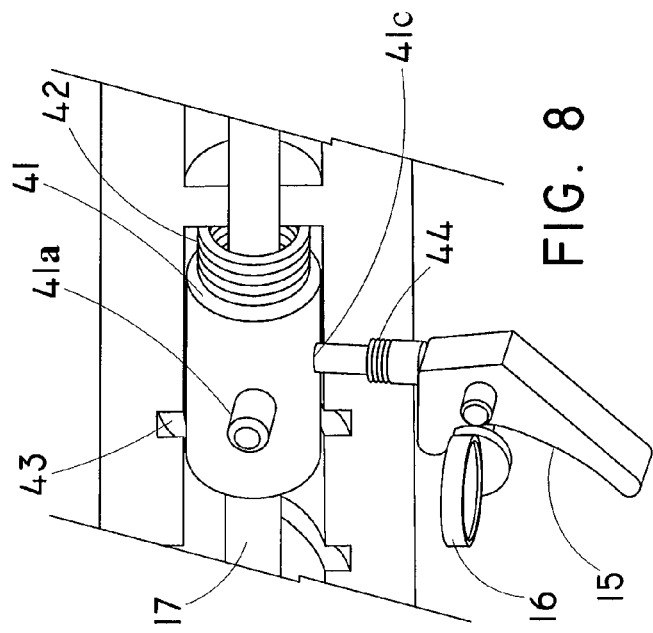

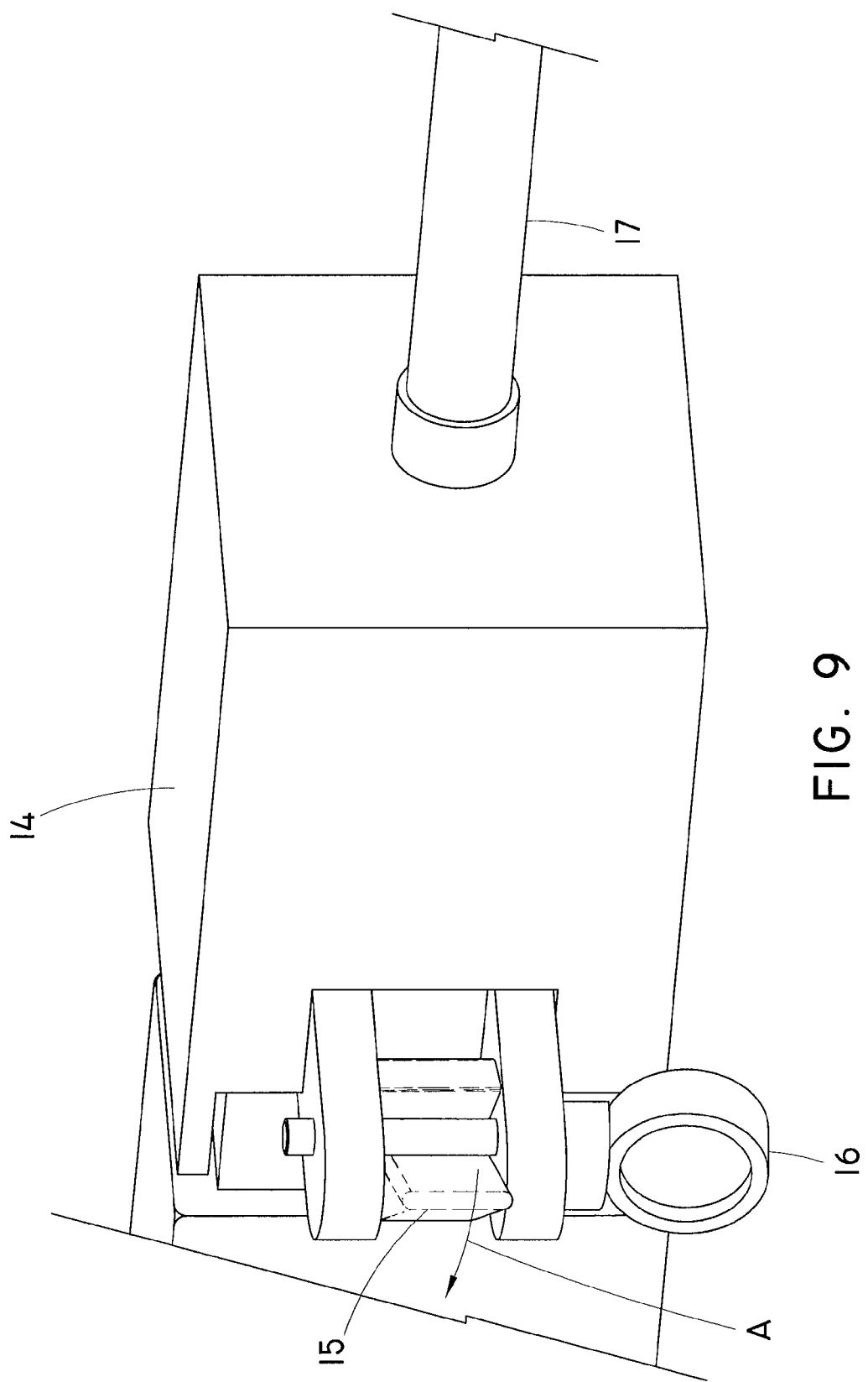

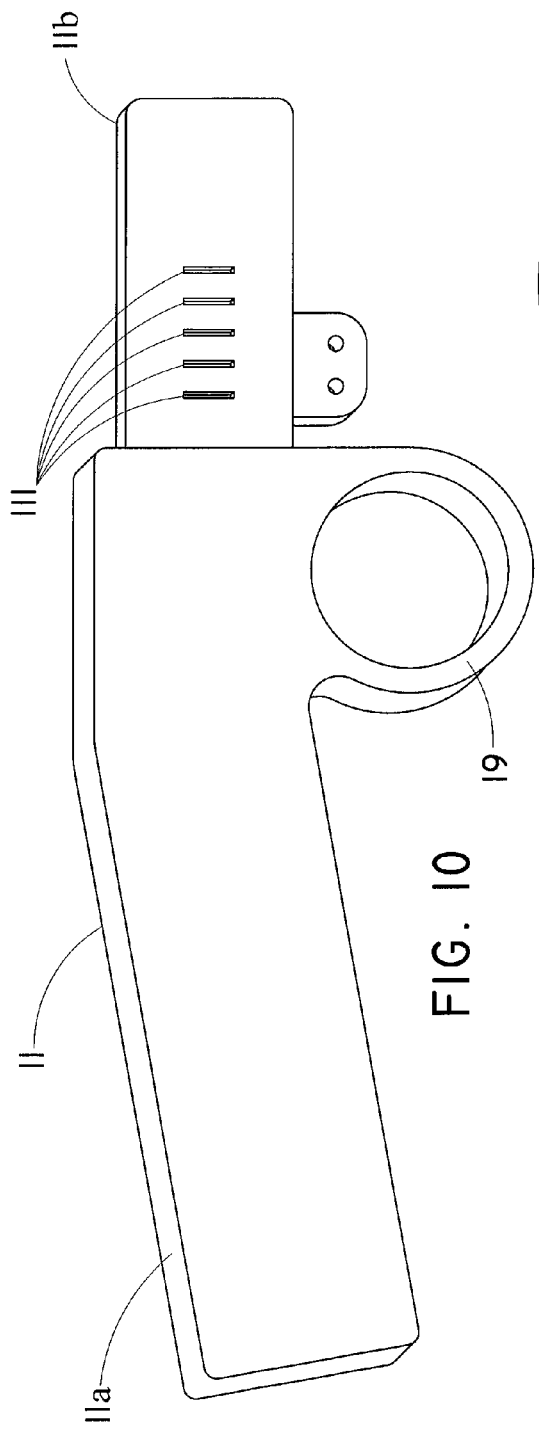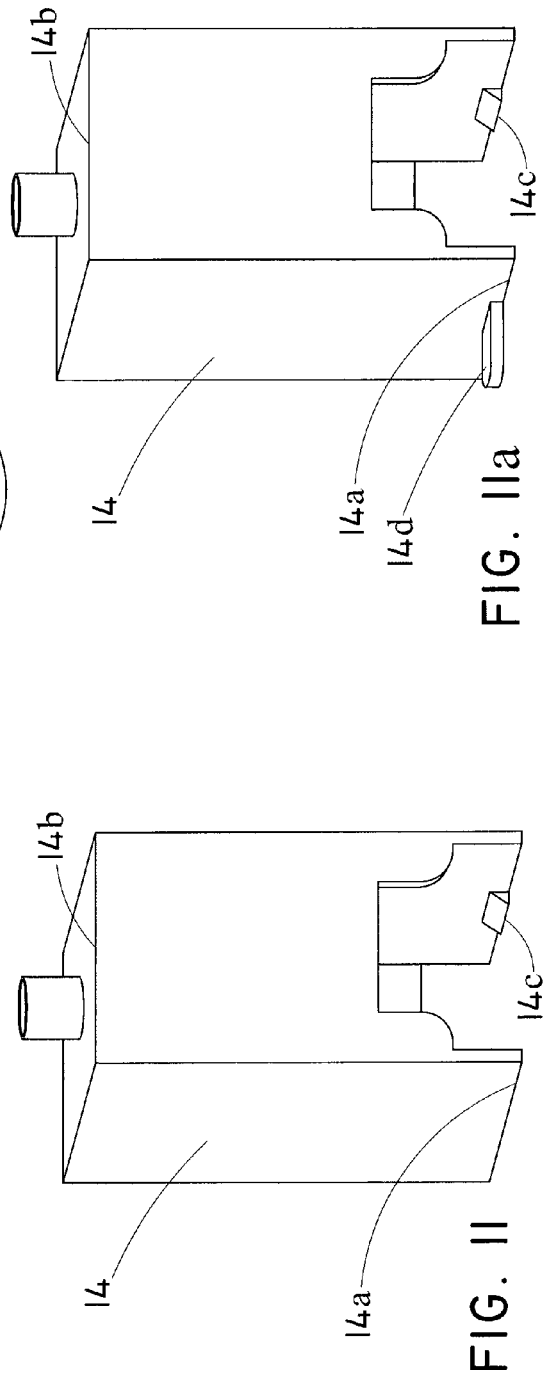

CORING TISSUE BIOPSY NEEDLE AND METHOD OF USE

RELATED APPLICATIONS

The present patent document claims priority to, the benefit of the filing date, and all other benefits under 35 U.S.C. § 119(e) and all other applicable statutes of U.S. Provisional Patent Application Ser. No. 61/425,106 filed Dec. 20, 2010, which is hereby incorporated by reference in its entirety.

FIELD OF THE INVENTION

The present invention relates to medical devices. More particularly, the invention relates to medical devices for taking a biopsy sample from a patient.

BACKGROUND OF THE INVENTION

Biopsies are important medical tests used to collect cells or tissue for examination so as to determine the presence, extent, or likelihood of disease, trauma, ailment, or for other diagnostic or therapeutic applications. Biopsies are generally painful procedures, and current devices used to collect samples suffer from many shortcomings. For example, the use of a single-ported device only permits the capture of a single sample per entry into the tissue region of interest, and the sample collected is generally of a small size resulting in the need for multiple entries or "sticks" so as to collect a sample of sufficient size. Indeed, current devices often result in a "blind" depth assessment because the biopsy device fails to accurately disclose the depth at which the sample gathering device is currently positioned. The blind depth assessment may also require multiple entries so as to collect a sufficient sample because the initial or subsequent entries underpass or overpass the sample sought. Collection devices also cause unnecessary trauma to the surrounding tissue by ripping or tearing the sample from its original dwelling. Additionally, the force needed to manually drive the collection device into the tissue causes unnecessary pain to the patient. Current devices also suffer from an increased risk of contaminating the sample when ejected as well as increasing the user's exposure to sharps. The result of the many shortcomings from current needle biopsy devices may also create an increased risk of infection and site morbidity, sample contamination, patient pain, discomfort, and healing time.

There exists a need in the art for a biopsy device that provides for an accurate, sufficiently-sized sample collected at a known location while presenting minimal damage to the surrounding collection location and providing less opportunity for contamination after collection. There is a need in the art for a low cost, disposable biopsy device.

BRIEF SUMMARY OF THE INVENTION

In a first aspect, a biopsy device is provided having an entry needle having a proximal portion and a distal portion, wherein the distal portion is sharpened; a coring cannula having a proximal portion, a distal portion, and a central lumen extending between the proximal portion and distal portion, wherein the distal portion is sharpened; wherein at least a portion of the entry needle is disposed within the coring cannula and at least a portion of the coring cannula and entry needle are in communication with a handle; wherein the handle comprises a means for simultaneously deploying rotationally and axially the coring cannula over the entry needle.

In a second aspect, a biopsy device is provided having a needle means configured for entering a tissue sampling region; a coring means disposed over the needle means and configured for collecting a tissue sample; a drive means operably connected to the needle means and the coring means, wherein the drive means is configured for simultaneously axially reciprocating and rotationally driving the coring means relative to the needle means; and a means for ejecting the tissue sample from the coring means.

In a third aspect a method for taking a tissue biopsy is provided, wherein the method includes providing a biopsy device comprising a coring cannula and an entry needle; positioning the entry needle over a sample region; deploying the coring cannula over the entry needle wherein the coring cannula simultaneously travels axially and rotates collecting a sample within at least a portion of a lumen of the coring cannula; removing the biopsy device; and ejecting the sample into a collection device.

BRIEF DESCRIPTION OF THE SEVERAL VIEWS OF THE DRAWINGS

The embodiments will be further described in connection with the attached drawing figures. It is intended that the drawings included as a part of this specification be illustrative of the embodiments and should in no way be considered as a limitation on the scope of the invention. Indeed, the present invention specifically contemplates other embodiments not illustrated but intended to be included in the claims.

FIG. 7 is a cross-sectional view of an exemplary housing handle;

FIG. 8 is a close-up partial cross-sectional view of an exemplary housing handle having component parts;

FIG. 9 is a perspective view of an exemplary depth-limiting cap and an exemplary safety pin;

FIG. 10 is a perspective view of an exemplary housing handle;

FIG. 11 is a perspective view of an exemplary depth-limiting cap;

FIG. 11a is an alternate perspective view of an exemplary depth-limiting cap;

DETAILED DESCRIPTION OF PRESENTLY PREFERRED EMBODIMENTS

Figure 1:
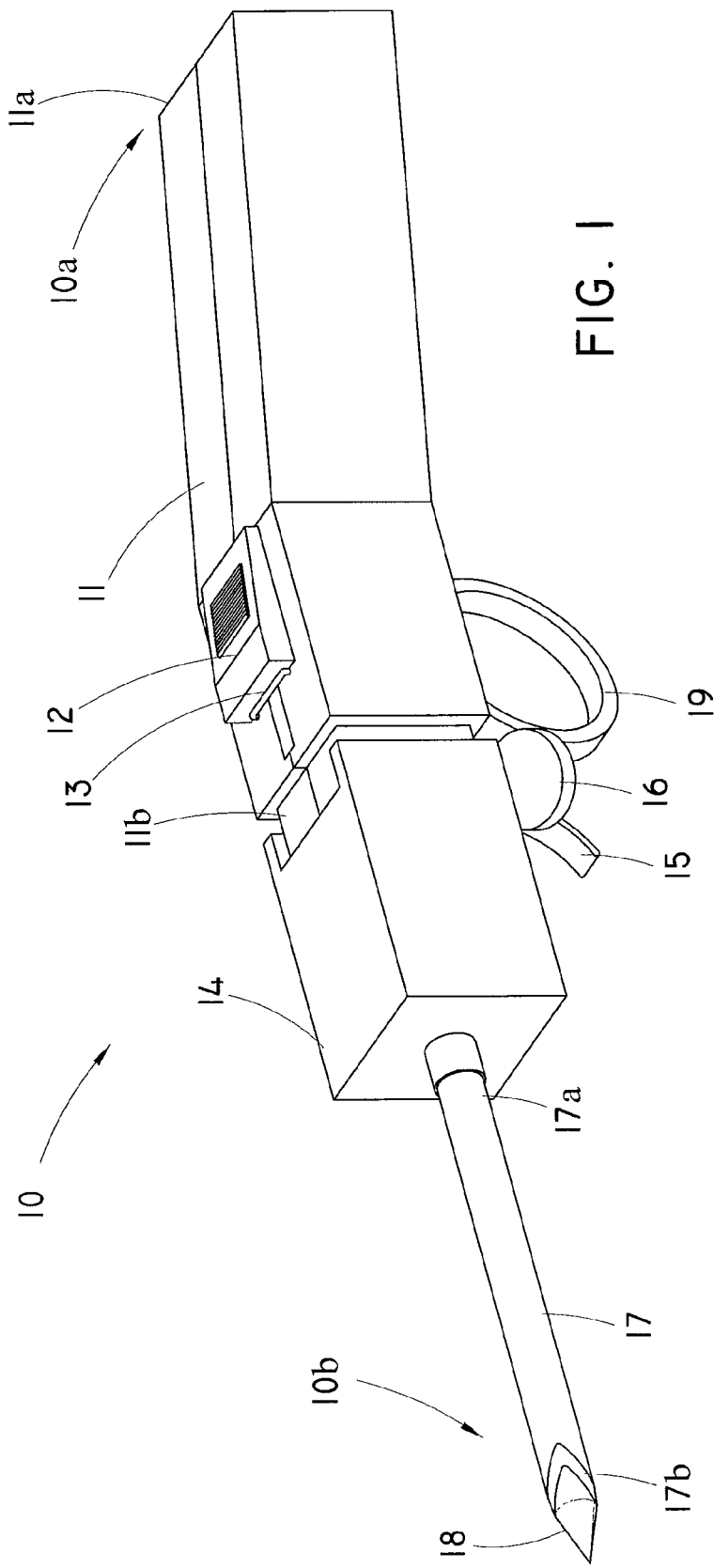
FIG. 1 is a perspective view of an exemplary biopsy device.

The exemplary embodiments disclosed herein provide coring tissue biopsy needle apparatuses and methods for collecting a biopsy sample from a patient. The present invention is not limited to any particular type of collection material; it is contemplated that the device can collect material, including but not limited to, tissue, muscle, and bone. Furthermore, the present invention is not limited for use within any particular part of the body or for use with humans.

The present invention is not limited to those embodiments illustrated herein, but rather, the disclosure includes all equivalents including those of different shapes, sizes, and configurations, including but not limited to, other types of biopsy devices. The devices and methods may be used in any field benefiting from a biopsy device.

Unless otherwise defined, all technical and scientific terms used herein have the same meaning as commonly understood by one of ordinary skill in the art. In case of conflict, the present document, including definitions, will control. Preferred methods and materials are illustrated below, although apparatuses, methods, and materials similar or equivalent to those illustrated herein may be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

A more detailed description of the embodiments will now be given with reference to FIGS. 1-15. Throughout the disclosure, like reference numerals and letters refer to like elements. The present invention is not limited to the embodiments illustrated; to the contrary, the present invention specifically contemplates other embodiments not illustrated but intended to be included in the claims.

FIG. 1 is a perspective view of an exemplary biopsy device 10 having a proximal portion 10a and a distal portion 10b. Biopsy device 10 is used to collect cells or tissue for examination so as to determine the presence, extent, or likelihood of disease, trauma, ailment, or for other diagnostic or therapeutic applications. Biopsy device 10 is held by proximal portion 11a of handle 11, and finger ring 19 provides for increased control of biopsy device 10 during use.

Biopsy device 10 comprises a means for entering a sample region SR including an entry needle 18 initially extending out from distal portion 17b of coring cannula 17. Entry needle 18 is a needle having a sharp point for penetrating skin, tissue, muscle, or other organic material in such a way that it reduces trauma to the surrounding area by piercing that to which the pointed end is directed. It is contemplated that entry needle 18 is machine ground to a desired sharpness such that it is able to efficiently and easily pierce organic material without using excessive force. It is contemplated, although not required, that for collecting muscle tissue, entry needle 18 may be about an 8 to 12 gauge needle.

Coring cannula 17 is a hollow tube having a beveled 17c distal portion 17b machine or hand ground to about 10-degree to 25-degree angles; other tolerances are contemplated depending upon the sample desired. It is contemplated, although not required, that for collecting muscle tissue, lumen 17d of coring cannula 17 be just larger than the outer diameter of entry needle 18.

Entry needle 18 and coring cannula 17 are contemplated to being of any size and shape suitable for retrieving a suitable sample size, and they can be manufactured in whole or in part from stainless steel or other suitable medical-grade materials, including echogenic and other materials that may or may not provide for visualization under fluoroscopy, x-ray, ultrasound, or MRI using known techniques.

Proximal portion 17a of coring cannula 17 passes through depth-limiting cap 14, located at distal portion 11b of handle 11, for limiting the tissue-depth into which coring cannula 17 initiates boring, and is further housed in cannula housing 71 (as illustrated in FIG. 7). Pulling trigger 15 causes coring cannula 17 to rotationally bore into the sample sought until it reaches the depth allowed by its stroke length, in other words, the length set by the entirety of the thread grooves 43 as illustrated in FIGS. 4 and 7.

Figure 15:
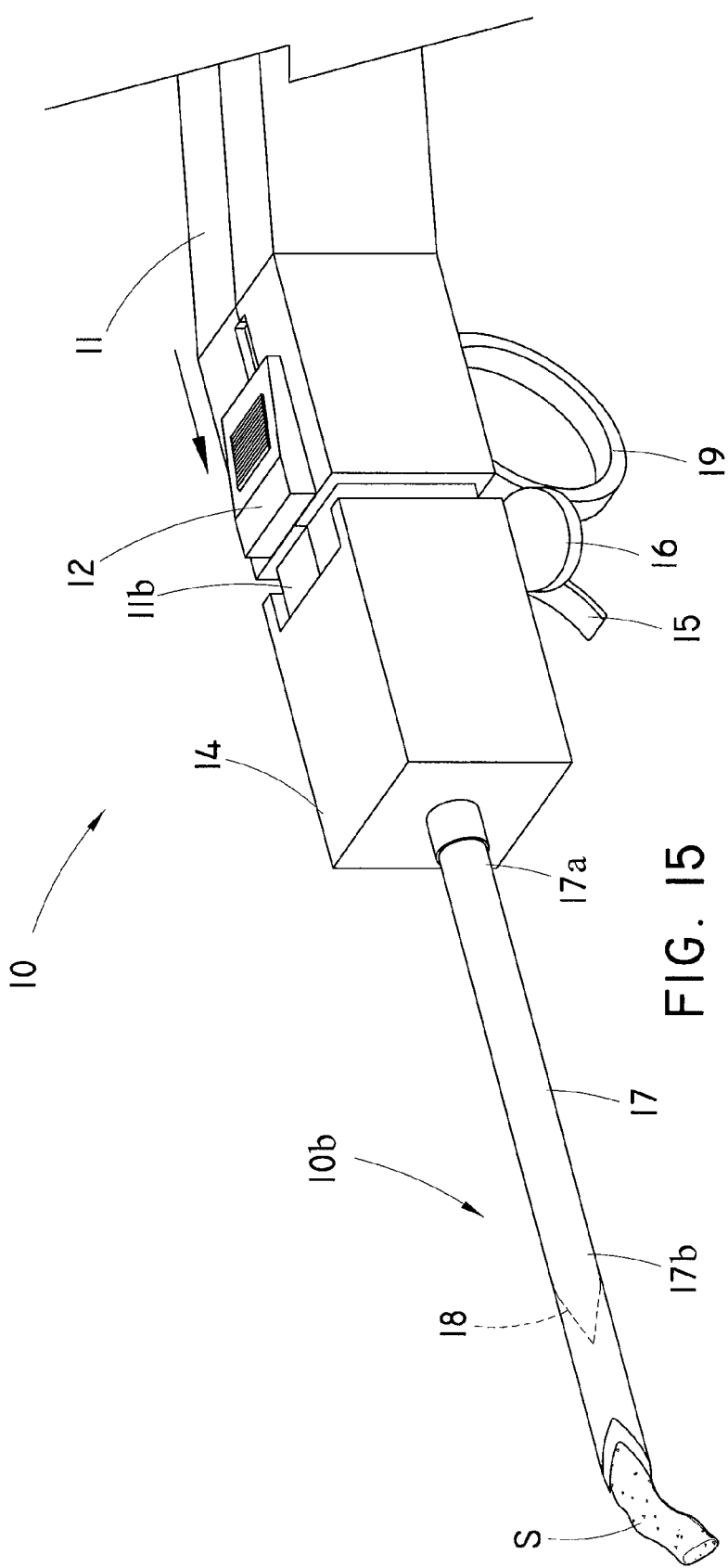
FIG. 15 is a view of an exemplary biopsy device ejecting a sample.

As illustrated in FIGS. 1 and 8, safety pin 16 engages pin entry point 41c of hub 41 to provide a means for preventing the unintentional boring and engagement of trigger 15 and deployment of coring cannula 17. As illustrated in FIGS. 4 and 15, after sample is collected, needle slider button 12 ejects sample S stored in coring cannula 17 by the axial reciprocating movement of entry needle 18 towards distal end 17b of coring cannula 17. Safety staple 13, as illustrated in FIG. 4, provides a means for preventing the unintentionally engagement of needle slider button 12 and ejection of a sample.

Figure 3:
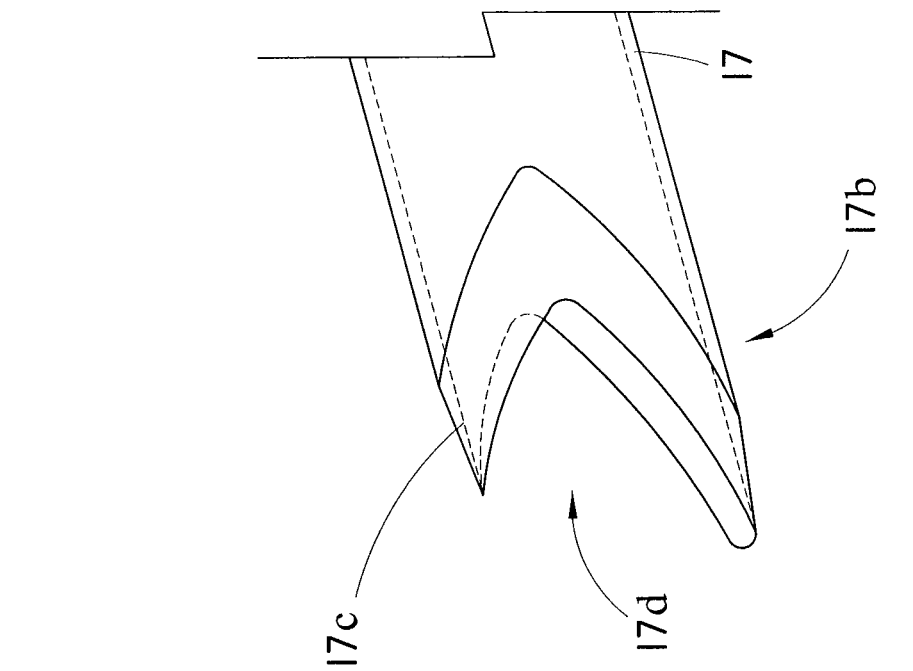
FIG. 3 is a partial perspective view of an exemplary coring cannula.
Figure 2:
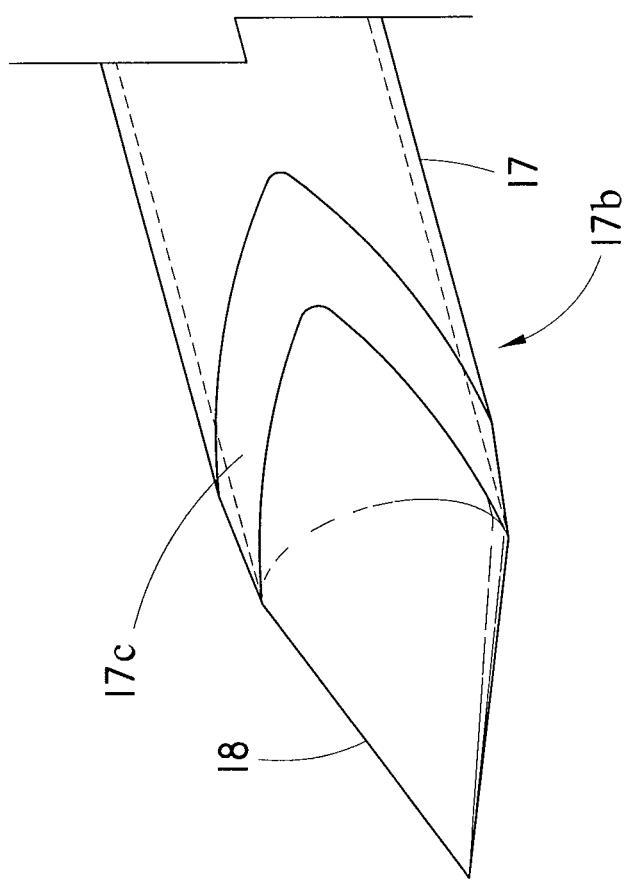
FIG. 2 is a partial perspective view of an exemplary entry needle and an exemplary coring cannula.
Figure 12:
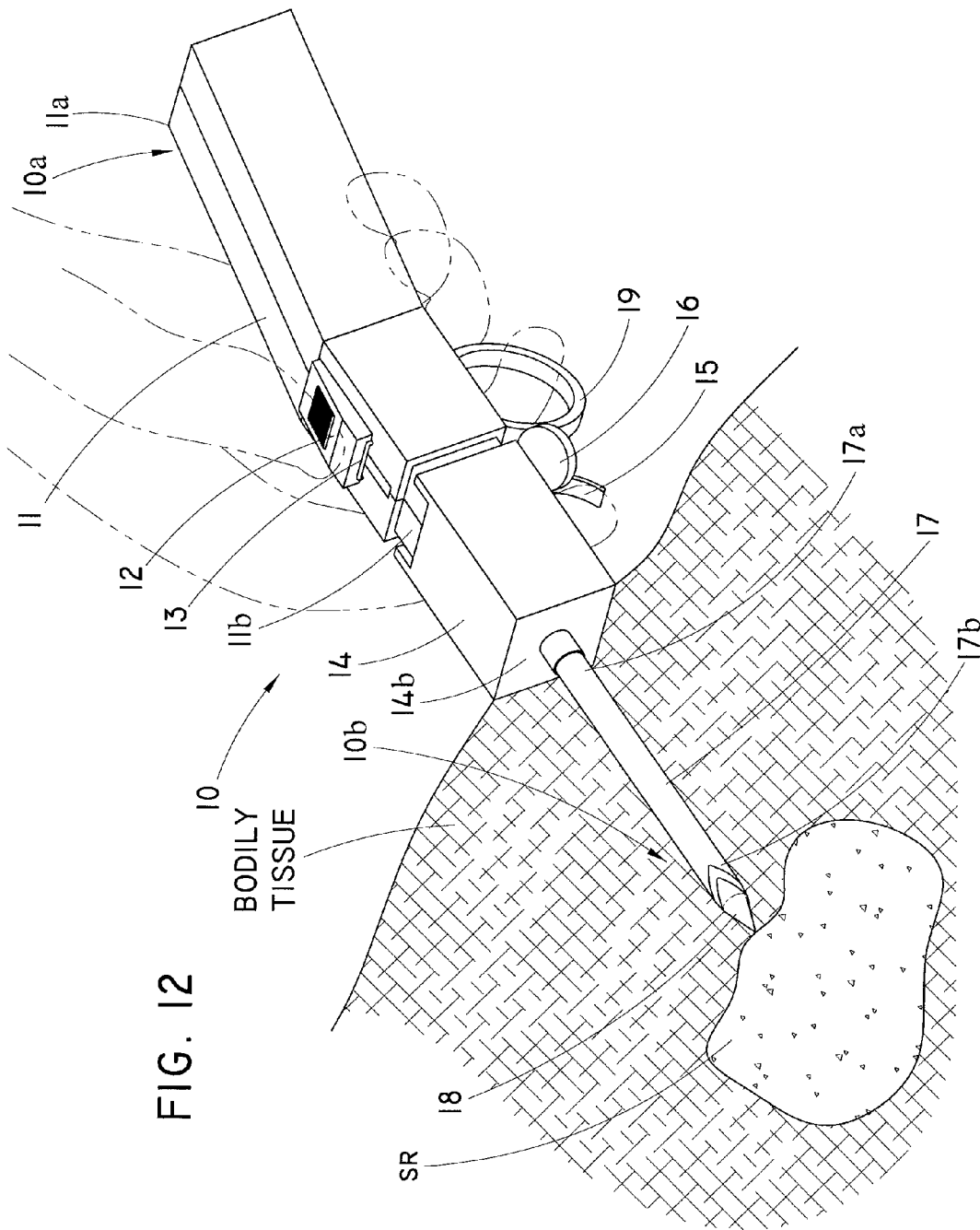
FIG. 12 is a view of an exemplary biopsy device in use before coring cannula deployment.
Figure 13:
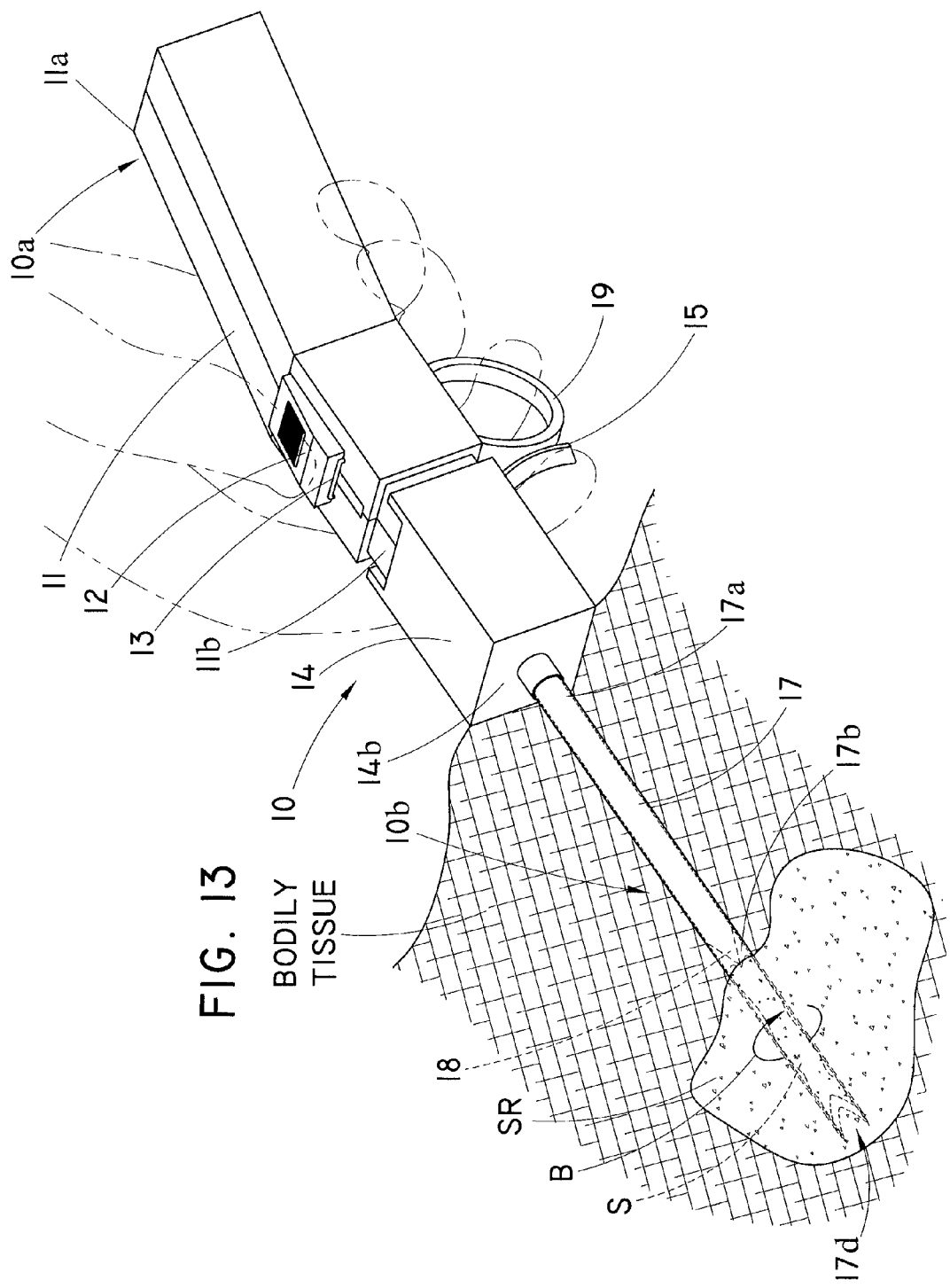
FIG. 13 is a view of an exemplary biopsy device in use after coring cannula deployment.
Figure 14:
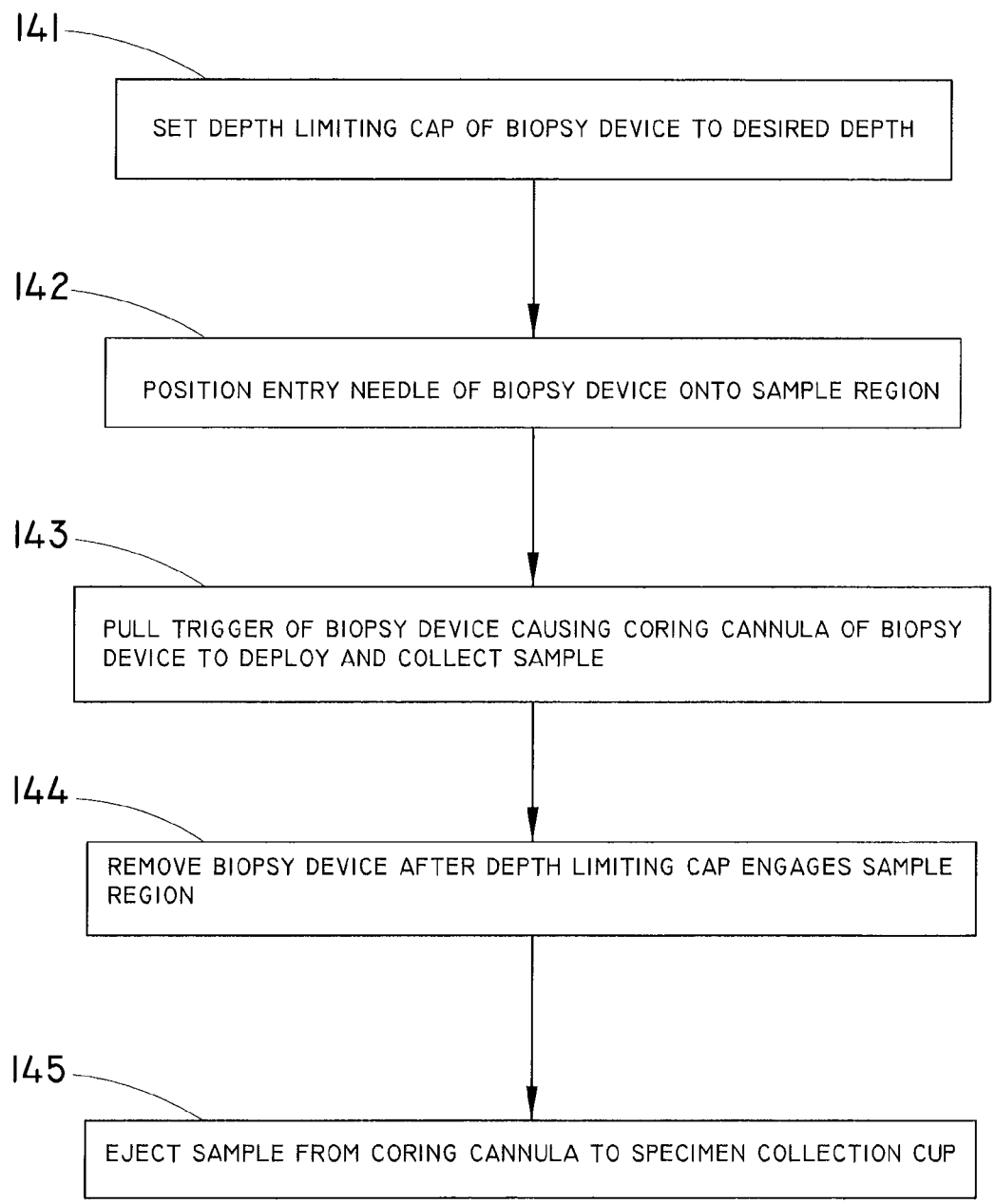
FIG. 14 is a method for using a biopsy device.

As illustrated in FIGS. 12 and 14, sample S is collected by extending entry needle 18 from distal portion 17b of coring cannula 17 to a depth at which the biopsy is to commence by having tissue engage distal portion 14b of depth limiting cap 14. The user sets a means for limiting the depth into which a sample can be retrieved, such as a depth-limiting cap 14, to the desired depth for initiating the bore and positions entry needle 18 towards sample region SR, the area from where the sample is to be collected 141. A user's finger is directed through ring 19 for added control, and safety pin 16 is released so that trigger 15 can be pulled, deploying coring cannula 17 causing it to simultaneously rotate (as illustrated by arrow B in FIG. 13) and move axially in the distal direction 17b into the sample to be collected 142, 143. As illustrated in FIGS. 2 and 3, distal portion 17b of coring cannula 17 has a sharpened leading edge to aid in the efficient boring of tissue with minimal damage to the surrounding tissue.

Figure 4:
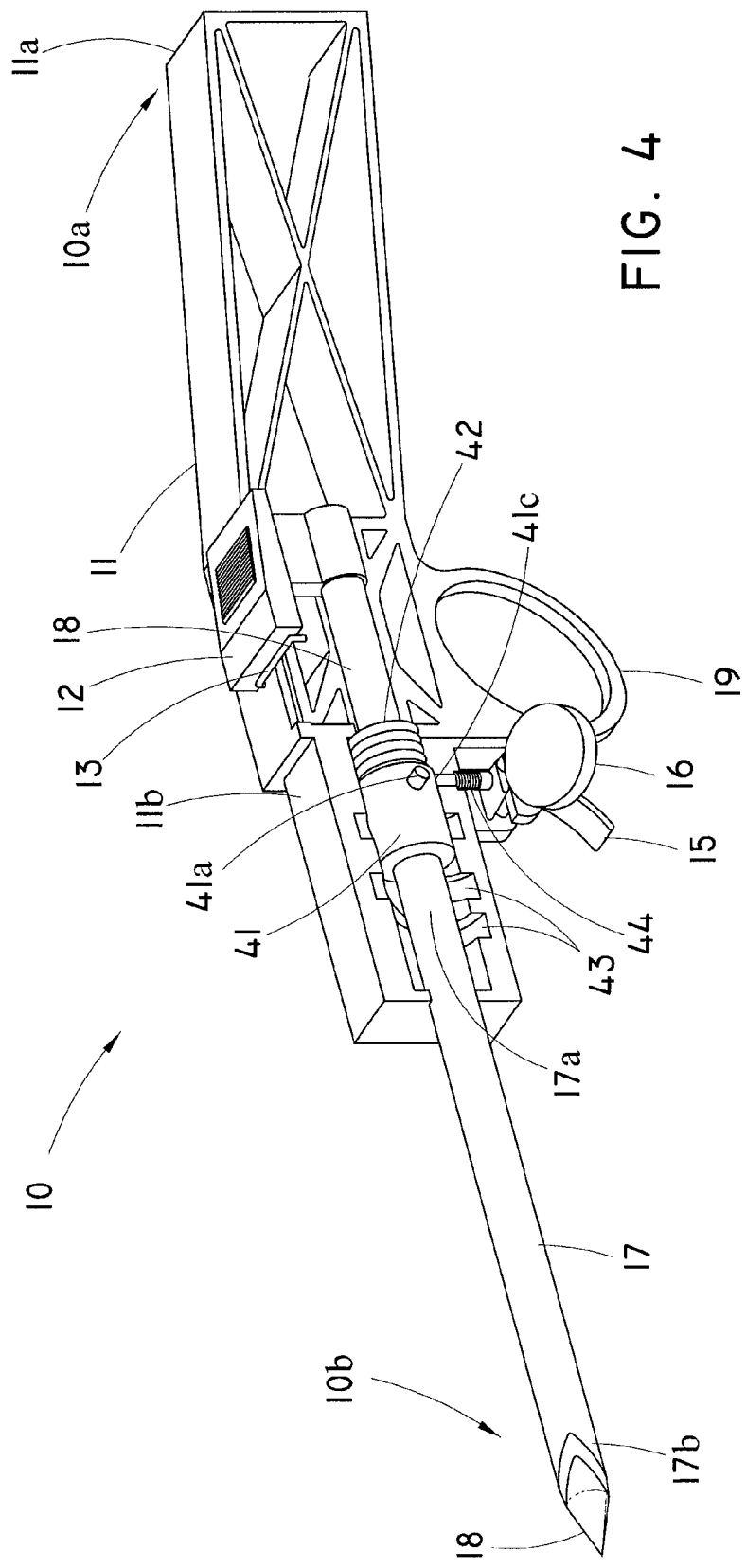
FIG. 4 is a partial cross-sectional view of an exemplary biopsy device.
Figure 6:
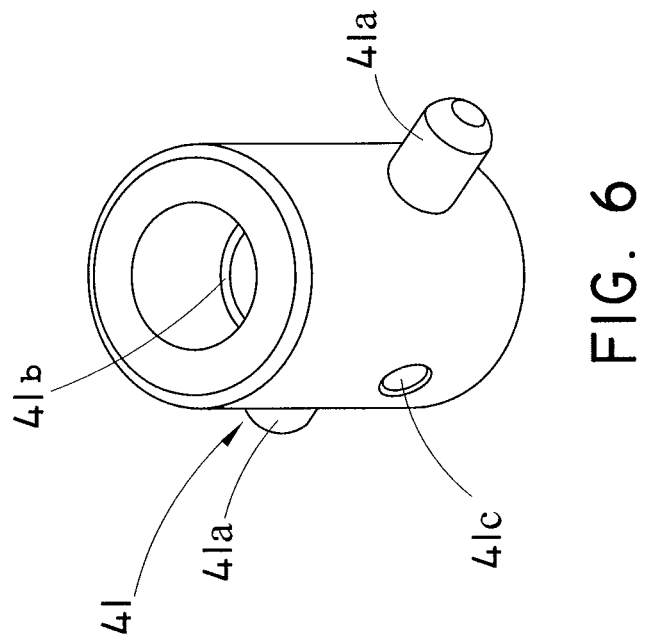
FIG. 6 is a top view of an exemplary hub.
Figure 5:
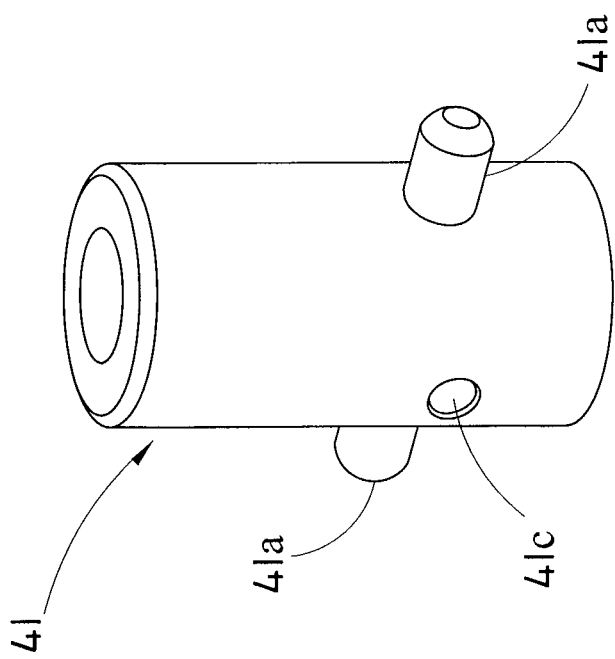
FIG. 5 is a perspective view of an exemplary hub.

The exemplary biopsy device 10 includes means for simultaneously boring axially and rotationally into the sample region SR such as those means illustrated in FIGS. 4, 5, and 6 wherein coring cannula 17 is fixedly attached to hub 41 having nubs 41a that are in communication with thread grooves 43 within distal portion 11b of handle 11. More particularly, as illustrated in FIGS. 4, 7, and 8, when trigger 15 (which engages hub 41 at trigger pin entry point 41c) is pulled, trigger 15, having a cam action, releases trigger pin-spring assembly 44 from trigger pin entry point 41c of hub 41 causing drive spring 42 to expand, push forward, and unwind into its biased form. This causes hub 41

(also illustrated in FIGS. 5 and 6) to move axially and rotationally as nubs 41a engage and follow thread grooves 43 for a linear travel length of about 2 cm (although other lengths are contemplated depending upon the need of the biopsy, sample, and patient), which in turn causes coring cannula 17, which is engaged with shoulder 41b of hub 41, to also move simultaneously axially forward and rotate—all without the user having to contort his/her hand or apply excessive force to sever the tissue. Additionally, because coring cannula 17 bores using both axial and rotational movement in a fluid, mechanical, and automated means, it reduces trauma to surrounding tissue that typically occurs from standard collection techniques.

The simultaneous axial and rotational movement of coring cannula 17 provides a means for collecting a sample by boring into the sample to be collected at a known rate and depth as set by the thread pitch of thread grooves 43. The thread pitch of thread grooves 43 and drive spring's 42 axial force can be altered to permit coring cannula 17 to travel and bore at various depths and into a variety of materials, including but not limited to, muscle, bone, and tissue. Ideally, for coring muscle tissue, the thread pitch is manufactured to travel about 2 cm over about 3 to 4 turns (0.5 cm or ⅛ cm per turn) but other tolerances are contemplated depending upon the sample needed.

The depth coring cannula 17 initiates boring is set by depth-limiting cap 14 that enables the user to set a precise boring starting depth rather than take a sample blindly which can result in under-passing or over-passing the tissue of interest thus subjecting the patient to additional sticks, trauma, and risk of infection. Accordingly, the user is able to retrieve a sample from a known sample region SR on the first attempt, rather than having to stick a patient multiple times to retrieve the sample sought. As illustrated in FIGS. 1, 9, 10, and 11, depth-limiting cap 14 has ratchets 14c at proximal portion 14a that engage ratchet grooves 111 on distal portion 11b of handle 11. Ratchet grooves 111 are set at known distances apart of about 2-3 mm but other distances are contemplated based on the needs of the patient and depth of sample material sought. User adjusts ratchets 14c of depth-limiting cap 14 to engage ratchet grooves 111 to the depth needed for coring cannula 17 to initiate boring. As illustrated in FIG. 9, safety pin 16 can be removed, permitting trigger 15 to be moved in the direction of arrow A. As illustrated in FIG. 13, after trigger 15 is pulled, coring cannula 17 simultaneously rotates (as illustrated by arrow B) and moves axially. Cored tissue sample S is automatically cut and stored in lumen 17d of coring cannula 17 as coring cannula 17 bores simultaneously rotationally and axially through sample region SR. Because a sufficient portion of the inner space of coring cannula 17 is utilized via central lumen 17d extending throughout, biopsy device 10 is able to capture more tissue in an improved and efficient manner in one stick.

The exemplary biopsy needle 10 also includes a means for ejecting a sample such as entry needle 18 being fixed to needle slider button 12 which remains in a fixed position relative to handle 11 during the biopsy procedure. As illustrated in FIG. 15, after sample S is collected, biopsy device 10 is pulled out of the sample region SR, safety staple 13 is removed from biopsy device 10 which permits needle slider button 12 to be advanced distally 11b to eject tissue sample S stored in coring cannula 17 into a specimen cup or collection container, 144, 145. The means for ejecting limits the physician's exposure to sharps and limits the potential for contaminating the sample collected.

Biopsy device 10 can be manufactured by standard means of plastic injection molding or by other means. It is contemplated that biopsy device can be used by physicians, surgeons, or other trained personnel in hospital, surgical suites, medical offices, or other clinical or research environments. Device 10 is contemplated for single use, although if sterilized, it can be used multiple times.

Neither biopsy device 10 nor any component part is limited to that which is illustrated herein. The present invention specifically contemplates other embodiments not illustrated but intended to be included in the claims. For example, handle 11 could be a variety of other shapes as opposed to that illustrated herein. For example, it is contemplated that handle 11 can be cylindrical, rectangular, or other shapes. Likewise, coring cannula 17 is not limited to that illustrated herein. For example, it is contemplated that coring cannula 17 can have a variety of other shapes including, but not limited to, that being of a trocar, triangular, and rectangular. Nubs 41a of hub 41 are not limited to that illustrated herein. For example, it is contemplated that hub 41 can be differently designed so as to achieve the same rotational and axial movement—such as, for example, hub being threaded rather than having nubs 41a. Depth-limiting cap 14 also is not limited to that illustrated herein. For example, depth-limiting cap 14 could be cylindrical and could also be threaded so as to provide more options for depth setting as opposed to having set ratchet grooves. As illustrated in FIG. 11a, depth-limiting cap may also include wings 14d to permit an alternate means of mid-procedure un-engagement of ratchets 14c should the need arise to adjust the depth needed.

It can be seen that the embodiments illustrated and equivalents thereto as well as the methods of manufacturer may utilize machines or other resources, such as human beings, thereby reducing the time, labor, and resources required to manufacturer the embodiments. Indeed, the discovery is not limited to the embodiments illustrated herein, and the principles and methods illustrated herein may be applied and configured to any biopsy device.

Those of skill in the art will appreciate that embodiments not expressly illustrated herein may be practiced within the scope of the present discovery, including that features illustrated herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages illustrated above are not necessarily the only advantages of the discovery, and it is not necessarily expected that all of the illustrated advantages will be achieved with every embodiment of the discovery.

What is claimed is:

1. A biopsy device comprising:
   an entry needle comprising a proximal portion and a distal portion, wherein the distal portion is sharpened;
   a coring cannula configured to bore into a tissue region and comprising a second proximal portion, a second distal portion, and a central lumen extending between the second proximal portion and the second distal portion, wherein the second distal portion comprises an angled distal tip having an asymmetrical profile that is sharpened and comprises a beveled distal edge configured to excise tissue upon both axial and rotational movement thereof, the beveled distal edge comprising a plurality of pointed peaks disposed on opposite sides of the asymmetrical profile alternating between a plurality of curvilinear cutting edges;

wherein at least a portion of the entry needle is disposed within the coring cannula and at least a portion of the coring cannula and entry needle are in communication with a handle; and wherein the handle comprises a means for simultaneously deploying rotationally and axially the coring cannula over the entry needle to extend the second distal portion of the coring cannula distally beyond the distal portion of the entry needle, the means for simultaneously deploying rotationally and axially the coring cannula over the entry needle comprising a unitary hub fixedly connected to the coring cannula, and a helical groove fixedly connected to the handle, the hub being in communication with and movable along the helical groove, wherein movement of the hub along the helical groove causes the coring cannula to simultaneously rotate and axially reciprocate along a helical pathway relative to the entry needle, the handle and a tissue sample, and wherein the handle further comprises a drive coil spring that is movable between a compressed first axial length and an elongated second axial length, wherein the spring is directly connected to a proximal end of the hub, and wherein the drive spring is biased to assume the elongated second axial length to axially drive the proximal end of the hub along the helical pathway.

2. The biopsy device of claim 1 further comprising a depth-limiting cap in communication with the handle and the coring cannula configured to set a depth at which boring initiates.

3. The biopsy device of claim 1 further comprising a safety pin configured to prevent an unintentionally deploying of the coring cannula over the entry needle.

4. The biopsy device of claim 1 further comprising a slider button in communication with the entry needle configured to eject the tissue sample via an axial movement of the entry needle relative to the coring cannula and the handle.

5. The biopsy device of claim 1 wherein the handle further comprises a ring configured to receive a finger for holding.

6. A biopsy device comprising:

a needle configured for entering a tissue sampling region, the needle comprising an elongate shaft having a constant cross-section;

a coring cannula disposed over the needle and configured for collecting a tissue sample, the coring cannula having an angled distal tip having an asymmetrical profile comprising a plurality of spaced apart distal cutting points and a beveled distal cutting edge, the plurality of spaced apart distal cutting points being disposed on opposite sides of the asymmetrical profile and extending distally of adjacent portions of the beveled distal cutting edge;

a drive mechanism operably connected to the needle and the coring cannula, wherein the drive mechanism is configured for simultaneously axially reciprocating and rotationally driving the coring cannula along a helical pathway relative to the needle and the tissue sample, the drive mechanism comprising an axially expandable drive coil spring directly connected to a unitary hub, the hub being affixed to the coring cannula, wherein the hub engages a helical thread groove disposed on an interior surface of a handle, wherein movement of the hub along the helical thread groove causes the coring cannula to simultaneously rotate and axially reciprocate along the helical pathway relative to the handle, and wherein the movement of the hub is caused by axial expansion of the drive coil spring only; and an ejection mechanism configured for ejecting the tissue sample from the coring cannula.

7. The biopsy device of claim 6 wherein the handle comprises a movable cap configured for limiting a depth at which the coring cannula initiates boring into the tissue sample.

8. The biopsy device of claim 6 wherein the needle configured for entering the tissue sampling region comprises a gauge of 8 to 12.

9. The biopsy device of claim 6 wherein the distal tip has at least one angle comprising 10-degrees to 25-degrees.

10. The biopsy device of claim 6 wherein the coring cannula comprises a proximal portion and a distal portion, and a central lumen extending between the proximal portion and distal portion.

11. The biopsy device of claim 6 wherein the ejection mechanism comprises a slider button movably disposed on the handle, the slider button being in communication with the needle and configured to axially move the needle relative to the handle.

12. The biopsy device of claim 6 further comprising a safety pin removably coupled to the handle, the safety pin being configured for preventing an unintentional movement of the coring cannula relative to the handle.

13. The biopsy device of claim 6 further comprising a safety staple removably coupled to the handle, the safety staple being configure for preventing an unintentional movement of the needle relative to the handle.

14. A method for taking a tissue biopsy comprising: providing a biopsy device comprising a coring cannula and an entry needle movably disposed therein, the coring cannula having a distal end comprising an asymmetrical cutting profile having a pair of distal cutting points disposed on opposite sides of the asymmetrical cutting profile, each of the pair of distal cuttings points projecting distally relative to an adjacent curvilinear cutting edge disposed on either side thereof:

positioning a second distal end of the entry needle adjacent to a sample region;

axially expanding a drive coil spring to deploy the coring cannula over and beyond the second distal end of the entry needle and into the sample region, wherein the drive coil spring directly engages a proximal end of a unitary hub affixed to the coring cannula, and wherein the unitary hub and the coring cannula are configured to simultaneously travel axially and rotate along a helical pathway relative to the entry needle to collect a tissue sample within at least a portion of a lumen of the coring cannula and adjacent to the second distal end of the entry needle;

removing the biopsy device; and ejecting the tissue sample from the lumen of the coring cannula and into a collection device.

15. The method of claim 14 wherein a depth-limiting device of the biopsy device is set configured to limit a depth into which the coring cannula initiates travel into the sample region.

* * * * *

UNITED STATES PATENT AND TRADEMARK OFFICE
CERTIFICATE OF CORRECTION

PATENT NO. : 9,968,337 B2  
APPLICATION NO. : 13/325662  
DATED : May 15, 2018  
INVENTOR(S) : Haselby et al.

Page 1 of 1

It is certified that error appears in the above-identified patent and that said Letters Patent is hereby corrected as shown below:

In the Claims

In Column 8, Claim 15, Line 61, after "device of the biopsy device is", delete "set".

Signed and Sealed this
Tenth Day of September, 2019

Andrei Iancu
*Director of the United States Patent and Trademark Office*